(12) United States Patent
Van Rees

(10) Patent No.: US 6,251,431 B1
(45) Date of Patent: Jun. 26, 2001

(54) MOTH AND INSECT REPELLANT

(75) Inventor: Norman A. Van Rees, Kirkwood, MO (US)

(73) Assignee: Chemia Corporation, Maryland Heights, MO (US)

( * ) Notice: Subject to any disclaimer, the term of this patent is extended or adjusted under 35 U.S.C. 154(b) by 0 days.

(21) Appl. No.: 08/069,434

(22) Filed: Jun. 1, 1993

Related U.S. Application Data

(63) Continuation-in-part of application No. 07/882,272, filed on May 13, 1992, and a continuation-in-part of application No. 07/912,906, filed on Jul. 13, 1992.

(51) Int. Cl.[7] ................................................. A01N 25/08
(52) U.S. Cl. ........................................... 424/469; 424/488
(58) Field of Search ................................. 424/76.8, 76.3, 424/76.4, DIG. 10, 195.1, 409, 488; 514/60, 558

(56) References Cited

U.S. PATENT DOCUMENTS

| | | | |
|---|---|---|---|
| 2,691,615 | * | 10/1954 | Turner et al. .................... 424/76.3 |
| 3,490,742 | * | 1/1970 | Nichols et al. .................... 252/99 |
| 4,369,308 | * | 1/1983 | Trubiano ............................ 536/106 |
| 4,719,040 | * | 1/1988 | Traas et al. ............................ 512/4 |
| 4,755,377 | * | 7/1988 | Steer ................................ 424/76.4 |
| 4,812,445 | * | 3/1989 | Eden et al. .......................... 514/60 |

FOREIGN PATENT DOCUMENTS

486630 * 9/1977 (AU) ................................... 422/5

* cited by examiner

*Primary Examiner*—Gary Geist
(74) *Attorney, Agent, or Firm*—Armstrong Teasdale LLP

(57) ABSTRACT

A biodegradable insect repellant that breaks down in the presence of water to minimize solid waste, comprising a water soluble substrate substantially comprising foamed vegetable starch, and cedar oil carried in the substrate. The substrate is preferably made of corn and or potato starch. The cedar oil may be from about 0.01 to about 10 times the weight of the substrate. A coloring agent may optionally be provided in the cedar oil to impart color to the insect repellant. Because the substrate is made from a water soluble starch, it dissolves in water leaving little or no solid waste.

14 Claims, 1 Drawing Sheet

MOTH AND INSECT REPELLANT

CROSS REFERENCE TO RELATED APPLICATION

This application is a continuation-in-part of U.S. Pat. application Ser. No. 07/882,272, filed May 13, 1992, and of application Ser. No. 07/912,906, filed Jul. 13, 1992.

BACKGROUND AND SUMMARY OF THE INVENTION

This invention relates to a moth and insect repellant product for protecting clothing, and in particular to a biodegradable, environmentally safe insect repellant that dissolves in water, leaving minimal solid waste.

A wide variety of substances have been used to repel moths and insects to protect clothing during storage, including paradichloro benzene, and naphthalene. These chemicals are solids that sublime or evaporate to produce vapors that repel or kill moths and other insects. There are increasing concerns about the effects of such chemicals on the environment. There are concerns about the amount of volatile chemicals that are released, and about disposal of the containers and packages for these chemicals.

Cedar blocks and chips are more environmentally benign than most chemicals but they are generally less effective because of the low concentration of active ingredients.

The present invention relates to an improved moth and insect repellant and a method of manufacturing the improved repellant. Generally, the repellant according to the present invention comprises a water soluble substrate made from a foamed vegetable starch. The substrate is impregnated with cedar oil, that can evaporate from the substrate to repel insects. However, because the substrate is comprised of a foamed vegetable starch, it is water soluble and quickly breaks down when exposed to water. This not only reduces volume of solid waste that must be disposed of, but allows the spent repellant to be conveniently and safely disposed of in a sink or toilet. Because the substrate comprises substantially vegetable starches, the decomposition products are not harmful.

According to the method of making an insect repellant according to this invention, water soluble foamed vegetable starch particles are provided. These particles are treated with cedar oil that is absorbed by the particles.

Thus, the insect repellant of the present invention provides a ready, spill-proof source of an insect repellant substance to repel moths and other insects. The insect repellant is dry to the touch, and thus will not stain clothing. The insect repellant provides controlled, long-lasting release of cedar oil. When the cedar oil is spent, the insect repellant is conveniently and completely disposable in a sink or toilet. Even if the insect repellant is disposed of by conventional means, it quickly breaks down when exposed to water, and therefore does not take up space in landfills.

These and other features and advantages will be in part apparent and in part pointed out hereinafter.

DETAILED DESCRIPTION OF THE PREFERRED EMBODIMENT

An insect repellant according to the principles of this invention comprises a water soluble substrate substantially comprising a foamed vegetable starch. The starch is preferably corn starch, potato starch, or some combination of corn starch and potato starch. Of course, other suitable vegetable-derived starches could be used in addition to or instead of corn and/or potato starches. One suitable substrate material is BIO PAC™ Responsible Loose Fill Packaging from EverGreen Solutions, Inc., Minneapolis, Minn. Another suitable substrate material is ECO-FOAM™ extruded foam from American Excelsior, Inc., Arlington, Tex. These materials are substantially dry, rigid, open-celled foams consisting essentially of vegetable starches.

ECO-FOAM™ is composed of over 95% cornstarch from a special high-amylose hybrid corn which meets FDA food grade regulations, and due to the high starch content it decomposes easily in water. The remaining ingredient is a water-soluble organic polymer which meets FDA food contact regulations, and is a common ingredient in adhesives, textiles, and paper coatings. ECO-FOAM™ is manufactured with an extruder in a simple heat and steam process, and generally resembles polystyrene foam. The ECO-FOAM™ can be formed into chips or pieces, generally resembling polystyrene packing peanuts, or ECO-FOAM can be formed into large wafers and blocks, resembling polystyrene blocks.

Figure 1:
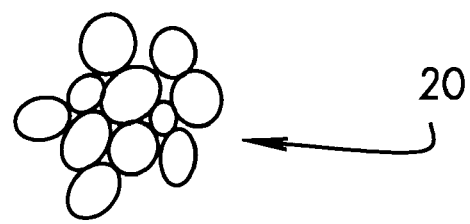
FIG. 1 is a drawing of water soluble foamed vegetable starch particles suitable for use as a substrate for an insect repellant in accordance with this invention.
Figure 2:
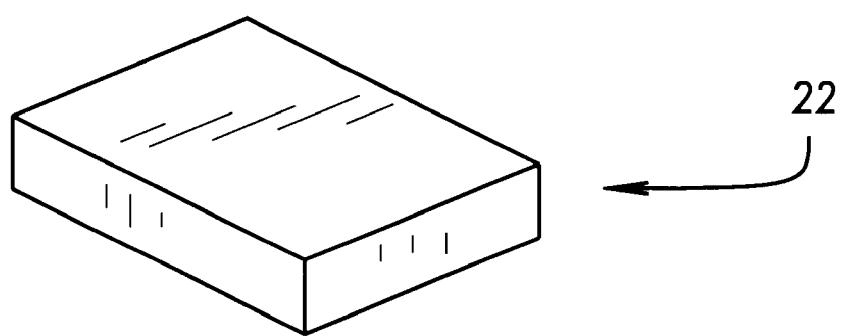
FIG. 2 is a drawing of a water soluble foamed vegetable wafer suitable for use as a substrate for an insect repellant in accordance with this invention.

The foamed starch substrate is a readily renewable resource. The substrate can be in the form of a foam sheet or other specific shape, for example the substrate may be in the form of particles or chips 20, shown in FIG. 1. Alternatively, the substrate may be in the form of a wafer 22, shown in FIG. 2.

Liquid cedar oil is infused into the substrate. Because of the foamed form of the substrate, the substrate readily absorbs between about 0.01 and about 10 times its weight in cedar oil, and preferably is infused with about 3 times its weight in cedar oil. The cedar oil is a naturally occurring, biodegradable substance.

A coloring agent can also be added to the cedar oil to impart a cedar color to the insect repellant. The color, is preferably, but not necessarily, a biodegradable substance.

The insect repellant can be stored in air tight containers or packages indefinitely, for example in a high density polyethylene package. The useful life of the insect repellant can be controlled by the amount of cedar oil absorbed into the substrate, the shape and surface area of the substrate, the air flow over the substrate, and the ambient temperature and humidity. The size and shape of the substrate can be selected to achieve the desired rate of release and insect repellant life.

The insect repellant is light weight and dry to the touch. It is rigid, yet resilient, resembling polystyrene packing peanuts in chip form, and polystyrene blocks in wafer form.

Because the foamed starch substrate is water soluble, when the useful life of the insect repellant is over, the substrate can simply be thrown away. As soon as the substrate is exposed to water, it will dissolve, leaving no solid residue behind. The resulting decomposition products are not harmful. The insect repellant can even be disposed of in a sink or toilet. The substrate dissolves immediately upon contact with the water, releasing any residual cedar oil. Thus disposal is easy, and environmentally responsible.

According to the method of this invention, a water soluble foamed starch substrate is provided. The substrate can be in the form of individual particles, a flat sheet, or any other convenient shape. The substrate is infused with liquid cedar oil.

EXAMPLE 1

The following is an example of the method of manufacturing an insect repellant according to this invention. 45.4 kilograms (100 pounds) of foamed vegetable starch BIO PAC™ Responsible Loose Fill Packaging chips from Ever-Green Solutions, Inc., Minneapolis, Minn., with a typical chip size of 3.2 mm×6.4 mm ×6.4 mm, are loaded into a 72 cubic foot (2 cubic meter) Marion Ribbon Blender. The Ribbon Blender is started and 136 kilograms (300 pounds) of red cedar oil, Virginia, is sprayed onto the chips through a fine tip atomizer nozzle. The chips are mixed for five minutes until the solution is completely absorbed. This imparts a pleasant cedar scent to the chips. The chips can be placed in an open container, to provide insect control in a drawer or closet as the cedar oil evaporates. When the cedar oil has dissipated to the extent that it is no longer effective, the insect repellant can be disposed of in the trash, where it dissolves on contact with water so that it does not add volume to a landfill, or more preferably the insect repellant is dumped in a sink or toilet, where it dissolves releasing any remaining cedar fragrance to freshen the sink or toilet.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A biodegradable insect repellant that breaks down in the presence of water to minimize solid waste, the insect repellant comprising:

a water soluble substrate substantially comprising a substantially dry, rigid, open-celled foam consisting essentially of vegetable starch; and cedar oil carried in the substrate.

2. The insect repellant according to claim 1 wherein the water soluble substrate comprises at least one of the group comprising corn starch and potato starch.

3. The insect repellant according to claim 1 wherein the cedar oil comprises 0.01 to 10 times the weight of the substrate.

4. The insect repellant according to claim 1 further comprising a coloring agent in the cedar oil carried in the substrate to impart color to the insect repellant.

5. The insect repellant according to claim 1 wherein the substrate is in the form of chips.

6. A method of making an insect repellant comprising the steps of:

providing a water soluble substrate made of a substantially dry, rigid, open-celled foam consisting essentially of vegetable starch; and causing a cedar oil to be absorbed into the substrate.

7. The method according to claim 6 wherein the cedar oil is between 0.01 and 10 times the weight of the substrate.

8. The method according to claim 6 wherein the substrate comprises at least one of the group comprising corn starch and potato starch.

9. A biodegradable insect repellant product that breaks down in the presence of water to minimize solid waste, the insect repellant comprising:

a water soluble substrate made of a substantially dry, rigid, open-celled foam consisting essentially of vegetable starch; and cedar oil carried in the substrate, which evaporates from the substrate to form insect repelling fumes;

the substrate being completely dissolvable in water so that the insect repellant can be disposed of down a sink or toilet, whereupon residual cedar oil will be released.

10. The insect repellant according to claim 9 wherein the water soluble substrate comprises at least one of the group comprising corn starch and potato starch.

11. The insect repellant according to claim 9 wherein the liquid fragrance comprises 0.01 to 10 times the weight of the substrate.

12. The insect repellant according to claim 9 further comprising a coloring agent in the cedar oil carried in the substrate to impart color to the insect repellant.

13. The insect repellant according to claim 9 wherein the substrate is in the form of chips.

14. A method of protecting clothing from insects using a biodegradable repellant comprising the steps of:

providing a substantially dry, rigid, open-celled foam substrate consisting essentially of vegetable starch, infused with cedar oil; allowing the cedar oil to volatilize from the substrate to form insect repelling fumes in the surrounding air; and dissolving the substrate in water when the cedar oil has substantially volatilized.

\* \* \* \* \*